United States Patent
Nemirovsky et al.

(10) Patent No.: US 9,518,953 B2
(45) Date of Patent: Dec. 13, 2016

(54) ION SENSITIVE DETECTOR

(75) Inventors: Yael Nemirovsky, Haifa (IL); Lior Gal, Yoqneam Illit (IL); Igor Brouk, Haifa (IL)

(73) Assignee: TECHNION RESEARCH AND DEVELOPMENT FOUNDATION LTD., Haifa (IL)

( * ) Notice: Subject to any disclaimer, the term of this patent is extended or adjusted under 35 U.S.C. 154(b) by 277 days.

(21) Appl. No.: 13/604,661

(22) Filed: Sep. 6, 2012

(65) Prior Publication Data
US 2013/0056353 A1     Mar. 7, 2013

Related U.S. Application Data

(60) Provisional application No. 61/531,713, filed on Sep. 7, 2011.

(51) Int. Cl.
    *G01N 27/414*      (2006.01)

(52) U.S. Cl.
    CPC .................. *G01N 27/4146* (2013.01)

(58) Field of Classification Search
    CPC ...................... G01N 27/414–27/4148
    USPC 204/416, 400, 419, 420, 418, 433; 257/253; 324/438, 446, 693
    See application file for complete search history.

(56) References Cited

U.S. PATENT DOCUMENTS

| | | |
|---|---|---|
| 4,133,735 A | 1/1979 | Afromowitz et al. |
| 4,180,771 A | 12/1979 | Guckel |
| 4,446,474 A | 5/1984 | Mizusaki et al. |
| 4,490,678 A | 12/1984 | Kuisl et al. |
| 5,309,085 A | 5/1994 | Sohn |
| 6,294,133 B1 * | 9/2001 | Sawada et al. ............ 422/82.01 |
| 6,617,190 B2 | 9/2003 | Chou et al. |
| 7,067,873 B2 | 6/2006 | King et al. |
| 7,081,195 B2 * | 7/2006 | Simpson et al. ........... 205/777.5 |
| 7,321,143 B2 | 1/2008 | Kunath et al. |
| 7,820,029 B2 | 10/2010 | Chou et al. |
| 2005/0241959 A1 * | 11/2005 | Ward et al. .................... 205/792 |

(Continued)

FOREIGN PATENT DOCUMENTS

| | | | |
|---|---|---|---|
| EP | 1363122 | 1/2008 | |
| GB | EP0065350 | * 4/1982 | ............. G01N 27/00 |

OTHER PUBLICATIONS

Juskova (PhD Thesis, Microfluidics and Nanotechnology for Bioanalytical applications).*

(Continued)

*Primary Examiner* — Gurpreet Kaur
(74) *Attorney, Agent, or Firm* — A.C. Entis-IP Ltd.

(57) ABSTRACT

An ISFET detector for determining concentration of a target ion in a fluid, the apparatus comprising: a semiconducting substrate comprising a source and a drain having source and drain electrodes respectively and a channel region between them in the substrate; an insulating material overlying the channel region; a gate electrode formed on the insulating material; a reference electrode electrifiable to establish an electric field in the channel region; an accumulator comprising a layer of material of thickness less than or equal to about 2 nm (nanometers) that accumulates a quantity of target ions responsive to concentration of the target ions in the fluid; a layer of a conducting material on which the accumulator is formed that is separate from the gate electrode; and a conducting element that electrically connects the layer of conducting material to the gate electrode.

10 Claims, 5 Drawing Sheets

(56) References Cited

U.S. PATENT DOCUMENTS

2010/0038243 A1* 2/2010 White et al. .................. 204/416
2011/0241081 A1* 10/2011 Rothberg et al. ............. 257/253
2011/0299337 A1* 12/2011 Parris et al. ............. 365/185.18

OTHER PUBLICATIONS

Guerra et al; Extended gate field effect transistor using V2O5 xerogel sensing membrane by solegel method; Solid State Sciences 11 (2009) 456e460; Received Apr. 28, 2008; received in revised form Jul. 24, 2008; accepted Jul. 28, 2008, Available online Aug. 8, 2008, Available online at www.sciencedirect.com.
Jakobson et al; Ion-Sensitive Field-Effect Transistors in Standard CMOS Fabricated by Post Processing; IEEE Sensors Journal, vol. 2, No. 4, Aug. 2002.
WO2009P20373, Oct. 1, 2009, Osaka et al.
XP002690046, Feb. 4, 2013, Aisaka et al.
European Search Report for corresponding European Application No. 12183552.4, filing date Sep. 7, 2012.

\* cited by examiner

ION SENSITIVE DETECTOR

RELATED APPLICATIONS

The present application claims benefit under 35 U.S.C. 119(e) of U.S. Provisional Application 61/531,713 filed Sep. 7, 2011, the disclosure of which is incorporated herein by reference.

TECHNICAL FIELD

Embodiments of the invention relate to ion sensitive field effect transistors.

BACKGROUND

Various types of chemical sensors for detecting a chemical analyte and determining its concentration are known and are used in an ever growing variety of applications. Chemical sensors may for example be used to determine concentrations of compounds in industrial processes, to detect bio-agents that may contaminate air or water, and to monitor substances in the body of a patient that may be relevant to the patient's health. The sensors may be based on any of a large gamut of technologies, variations of the technologies, and combinations of the technologies. The technologies include optical, acoustic, photoacoustic, electromechanical, electromagnetic, and/or electronic technologies to note just a few of the technologies that are employed by chemical sensors to generate signals responsive to the presence and concentrations of chemical analytes.

For many applications it is advantageous for a chemical sensor to be small, robust, characterized by fast and accurate response to changes in concentration of an analyte, and of course, to be relatively inexpensive. For example, it may be advantageous for a chemical sensor, conventionally also referred to as a biochemical sensors, to be configured for use in or on the body of a patient for relatively extended periods of time to monitor body analytes that may be relevant for diagnosing the patient's health. To function satisfactorily, such a biochemical sensor, should generally be relatively immune to damage by body fluids, be responsive in real time to changes in concentrations of a body analyte for which it is intended to be responsive, and to be sufficiently small so that its presence in or on the body is neither damaging nor uncomfortably obtrusive. Among analytes whose concentrations may be of interest for monitoring as indicators of a patient's health are by way of example the concentrations of sodium and calcium ions, $Na^+$ and $Ca^{2+}$, and the concentration (pH) of hydrogen ions, $H^+$.

Ion sensitive field effect transistors (ISFET), which were invented in 1970, are used to detect presence and concentrations of various species of ions, hereinafter target ions, in fluids into which they are placed. ISFETs have long been considered good candidates for providing small, fast, sensitive, accurate, and relatively inexpensive chemical and biochemical sensors. An ISFET typically comprises a reference electrode and a metal-oxide-semiconductor field effect transistor (MOSFET) modified to accumulate target ions the ISFET is intended to detect.

A conventional MOSFET comprises a source (S), a drain (D), and a conducting electrode referred to as a gate, formed in or on a semiconductor substrate, typically a silicon substrate. The source and drain may be n or p doped regions in the substrate, which is respectively p or n doped. The gate is formed generally from a metal or a polysilicon on a dielectric insulating layer, which overlies a region of the substrate between the source and the drain. The insulating layer is usually a layer of an oxide or nitride of the substrate material. A potential difference, "$V_{GS}$", applied between the gate and the substrate may be controlled to produce an electric field in the substrate that controls conductance of a conducting channel in a region, hereinafter referred to as a "channel region", of the substrate between the drain and the source. For a given potential difference, "$V_{DS}$", between the drain and the source, the potential difference $V_{GS}$ may therefore be used to control magnitude of a current, "$I_{DS}$," driven by $V_{DS}$ between the drain and the source.

In an ISFET, the modified MOSFET comprises a source and drain formed in a substrate of the ISFET and a dielectric insulator on which a gate electrode in a conventional MOSFET is formed, but may be missing a gate electrode. The dielectric insulator in the ISFET may be left exposed and configured to preferentially accumulate target ions from among other ions that may be present in a fluid into which the ISFET is placed. Alternatively, the modified MOSFET may have a gate electrode but in addition have formed on the gate electrode a layer of material tailored to preferentially accumulate the target ions. Hereinafter, the material in an ISFET that accumulates target ions may be referred to as an accumulator.

In operation, when the ISFET is placed in a fluid to detect presence and concentration of target ion in the fluid, the accumulator is exposed to the fluid and the target ions so that a quantity of the target ions may be accumulated by the insulator. To generate signals responsive to the accumulated target ions that may be used to determine concentration of the target ions in the fluid, at least one power supply powers the ISFET to provide a voltage, $V_{DS}$, between the drain and source of the ISFET's modified MOSFET and a voltage, "$V_{RS}$", between the reference electrode and the ISFET substrate. An electric field in the substrate that controls a current channel between the drain and source is a function of $V_{RS}$ and an electric field generated by a quantity of target ions from the fluid that may accumulate on the accumulator. For a given $V_{RS}$, and a given $V_{DS}$, current $I_{DS}$ in the ISFET is therefore a function of the quantity of target ions from the fluid that the accumulator accumulates.

Measurements of $I_{DS}$ or a known function of $I_{DS}$, hereinafter generically referred to as measurements of $I_{DS}$, are used to indicate the quantity of accumulated target ions. Under an assumption that the quantity of accumulated target ions is in dynamic equilibrium with, and changes in a known way with changes in concentration of target ions in the fluid, the measurements of $I_{DS}$ are used to estimate and track concentration of the target ions in the fluid. A measurements of $I_{DS}$ in a ISFET that is used to determine concentration of a target ion in a fluid may also be referred to hereinafter as a measurement of concentration, "$\rho_T$", of the target ion.

Whereas, as noted above, ISFETs have long been expected to find popular use as small, robust, and accurate chemical and biochemical sensors, they do not appear to have satisfied the optimism of their expectations. In operation, ISFETs have too often proven to be relatively unstable and labile sensors that exhibit long and short term drifts in sensitivity and require calibration at frequencies that limit their utility. In addition, for many applications it has been difficult to satisfactorily protect ISFETs from damage by components of fluids in which they are used

SUMMARY

An embodiment of the invention relates to providing a chemical detector, hereinafter also referred to as an "ISFET detector", which comprises an ISFET, is relatively insensitive to detector drift and damage by components of a fluid in which it is used, and may operate satisfactorily to provide measurements of a target ion with relatively infrequent calibration. The fluid may be a liquid or a gas.

The ISFET detector may comprise an ISFET having a source and a drain formed in a substrate, a gate electrode, and an ion accumulator in accordance with an embodiment of the invention formed on the gate electrode. Alternatively, the ISFET detector comprises an ion accumulator in accordance with an embodiment of the invention that is formed on a layer, hereinafter also referred to as an "accumulator base", of a conducting material, which is separated from, but electrically connected to the gate electrode.

The accumulator is formed having a thickness that contributes to moderating trapping of ions from the fluid by the accumulator. Optionally, the thickness is less than or equal to about 2 nm (nanometers). In an embodiment of the invention, thickness of the accumulator is less than 1 nm. Optionally, the accumulator comprises a monolayer of atoms or molecules and has a thickness about equal to that of the monolayer. Optionally, the accumulator is a native oxide of a conducting material on which the accumulator is formed.

Trapping of ions from a fluid by an ISFET accumulator generates relatively fixed, "trapped", charges in the accumulator that are not readily released to the fluid when concentration of target ions in the fluid decreases, and whose quantity may change over time, generally relatively slowly with time constants of a change that may equal several hours. As a result, trapping may contribute to short and long term drift in sensitivity of an ISFET that may necessitate frequent calibration of the ISFET to maintain its satisfactory operation. By providing an ISFET detector with an accumulator configured to moderate ion trapping, in accordance with an embodiment of the invention, the ISFET detector may be characterized by relatively reduced drift in sensitivity and therefore reduced frequency of calibration required to maintain the ISFET detector operating satisfactorily.

In an embodiment of the invention the ISFET detector comprises a controller that varies a reference voltage $V_{RS}$ that a power supply applies between a reference electrode and the substrate of the ISFET comprised in the ISFET detector to moderate leakage current in the ISFET. Leakage current between the reference electrode and the ISFET substrate may deposit varying amounts of charge in the ISFET or the accumulator that degrade accuracy and stability of measurements of the target ion concentrations.

In an embodiment of the invention, the controller reduces $V_{RS}$ substantially to zero or disconnects the reference electrode from the power supply for a period of time sufficiently long to enable leakage current charge accumulated on the accumulator to dissipate prior to acquiring a measurement of concentration of the target ion.

In an embodiment of the invention the ISFET detector comprises a switch controllable to electrically disconnect the accumulator base from the gate electrode for a period of time sufficiently long to enable leakage current charge accumulated on the accumulator to dissipate prior to acquiring a measurement of concentration of the target ion.

In an embodiment of the invention, an ISFET detector, which may hereinafter be referred to as a "dual ISFET", comprises a plurality of ISFETs comprising at least a first and a second ISFET and a reference electrode that is common to both the first and second ISFETs. The first and second ISFETs generate first and second output signals having a difference that may be used to provide a measurement of concentration of a given target ion in a fluid. In an embodiment of the invention, the first and second ISFETs are configured so that the first and second output signals have different responses to concentrations of the given target ion but substantially same responses to changes in first and second electric fields "$E_{RE}$" in their respective channel regions generated by a reference voltage $V_{RS}$ applied to the common reference electrode. The dual ISFET may comprise circuitry that generates a difference signal responsive to a difference between the first and second signals that is used to determine a concentration for the given target ion. The difference signal, and therefore the determined concentration of the given target ion, are substantially independent of drift in sensitivities of the first and second output signals that may be generated by changes in the first and second electric fields $E_{RE}$.

In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical features that appear in more than one figure are generally labeled with a same label in all the figures in which they appear. A label labeling an icon representing a given feature of an embodiment of the invention in a figure may be used to reference the given feature. Dimensions of features shown in the figures are chosen for convenience and clarity of presentation and are not necessarily shown to scale.

DETAILED DESCRIPTION

Figure 1A:
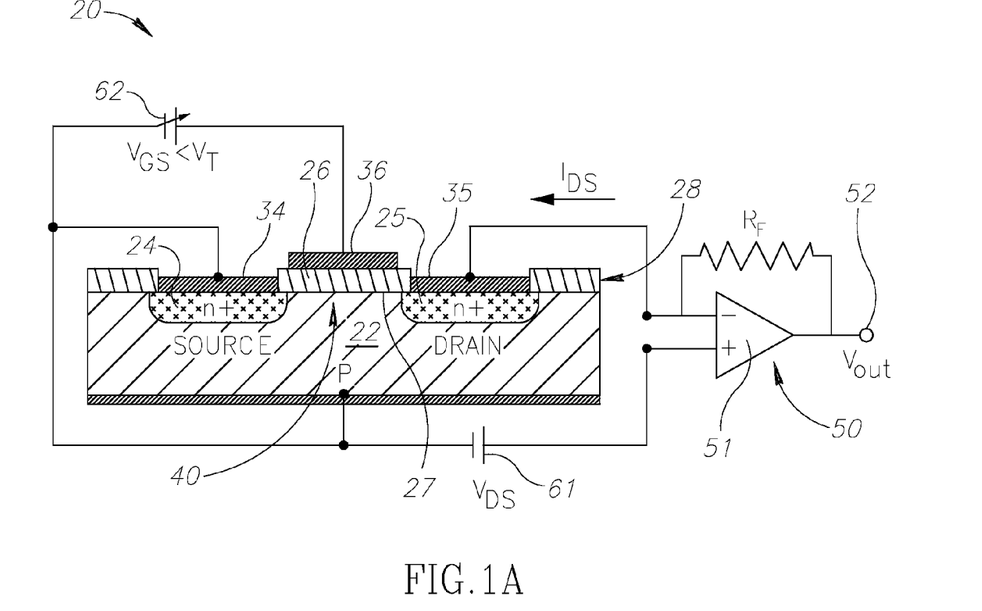
FIGS. 1A and 1B schematically illustrate a conventional FET and operation of the FET.
Figure 1B:
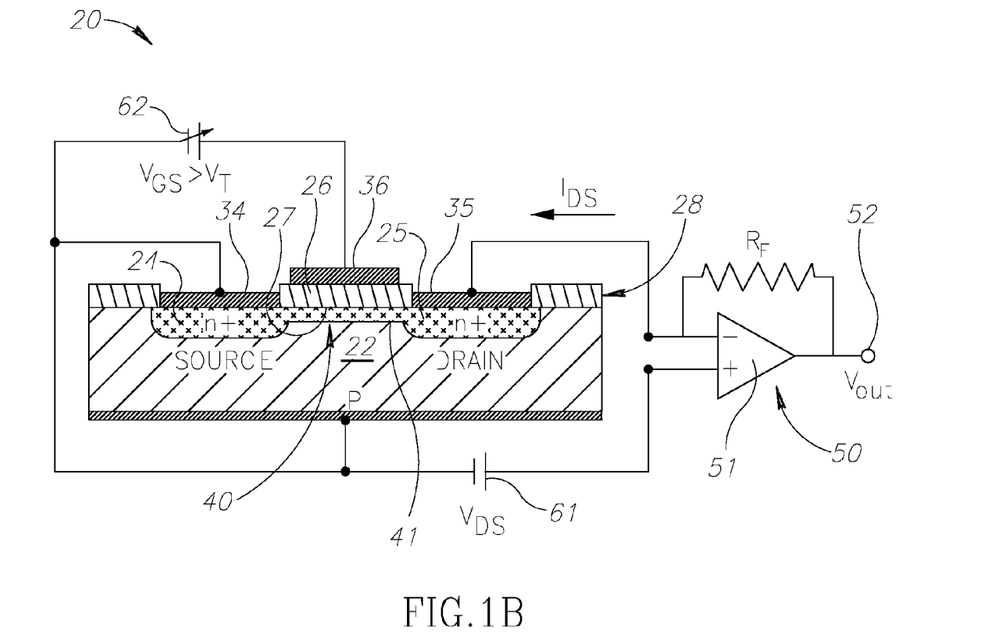

FIGS. 1A and 1B show schematic cross sections of a MOSFET 20 that illustrate operation of the MOSFET. MOSFET 20 comprises a substrate 22 light doped with acceptor, p, or donor, n, impurities that provide the substrate with positive (holes) or negative (electrons) majority charge carriers respectively, a source (D) region 24, and a drain (S) region 25. Source and drain regions 24 and 25 are formed in substrate 22 by heavily doping the regions with a same type of impurity to provide the regions with a same type of majority charge carrier, which has a charge opposite to that of the majority charge carrier in the substrate. By way of example, in FIGS. 1A and 1B and figures that follow, substrate 22 is assumed to be lightly doped with p acceptor impurities, and source and drain regions 24 and 25, are assumed to be doped with n, donor impurities.

Source and drain conducting electrodes 34 and 35 are formed on source and drain regions 24 and 25 respectively to provide electrical connection to the regions. A dielectric insulating layer 28 covers a "top" surface 27 of substrate 22 except where source and drain electrodes 34 and 35 are located. A conducting gate electrode 36 is formed on a portion 26, hereinafter also referred to as a "channel insulator", of insulating layer 28, which overlies a channel region 40, of substrate 22 between source 24 and drain 25.

For a given positive voltage $V_{DS}$ of drain 25 relative to source 24, a voltage $V_{GS}$ between gate electrode 36 and substrate 22 may be used to establish and control conductance of a current channel of electrons in channel region 40. When established, the current channel bridges drain 24 and source 25 and supports a current $I_{DS}$ driven by voltage $V_{DS}$ that flows from the drain to the source. In FIGS. 1A and 1B voltage $V_{DS}$ is provided by a power supply 61, and a controllable voltage $V_{GS}$ is provided by a power supply 62.

In general, for $V_{GS}$ less than a positive (for p-doped substrate 22) threshold voltage, "$V_T$", that characterizes MOSFET 20, an electron current channel in channel region 40 is non-existent. $V_T$ is a function of an energy band structure of substrate 22 and work functions of gate electrode 36 and substrate 22. For $V_{GS}$ equal to or greater than $V_T$, electrons in substrate 22 are attracted to and accumulate in channel region 40 close to channel insulator 26 to form an electron current channel that bridges source and drain region 24 and 25. FIG. 1A shows MOSFET 20 with $V_{GS}<V_T$ and absent a current channel between source 24 and drain 25. FIG. 1B schematically shows MOSFET 20 with $V_{GS}>V_T$ and a current channel 41 of electrons bridging source 24 and drain 25.

Conductance of current channel 41 is a function of a difference between $V_{GS}$ and $V_T$ and as $V_{GS}$ increases beyond $V_T$, conductance of the current channel increases. For a given voltage $V_{DS}$ between source 24 and drain 25, the current channel supports current $I_{DS}$ between the drain and the source. For $V_{DS}$ greater than or equal to a saturation voltage of MOSFET 20, current $I_{DS}$ is substantially independent of $V_{DS}$ and may be written as a function of a difference ($V_{GS}-V_T$).

For relatively large distances between source 24 and drain 25, current channel 41 may be considered a long current channel, and $I_{DS}$ may be approximated by a quadratic expression of the form $I_{DS}=\alpha(V_{GS}-V_T)^2$, where $\alpha$ is a constant. For a relatively short distance between source 24 and drain 25, current channel 41 may be considered a short current channel and $I_{DS}$ may be approximated by a linear expression of the form $I_{DS}=\beta(V_{GS}-V_T)$, where $\beta$ is a constant. MOSFET 20 may be produced having a relatively short distance between source 24 and drain 25 if the MOSFET is manufactured using a small line width manufacturing processes.

In FIGS. 1A and 1B MOSFET 20 is coupled to a readout circuit 50 comprising an operational amplifier 51 and feedback resistor $R_F$ that has an output terminal 52. The readout circuit maintains voltage between source 24 and drain 25 substantially equal to $V_{DS}$ provided by power supply 61 and generates an output voltage $V_{out}$ at output terminal 52 that is a function of, and may be used to indicate, $V_{GS}$.

Figure 2A:
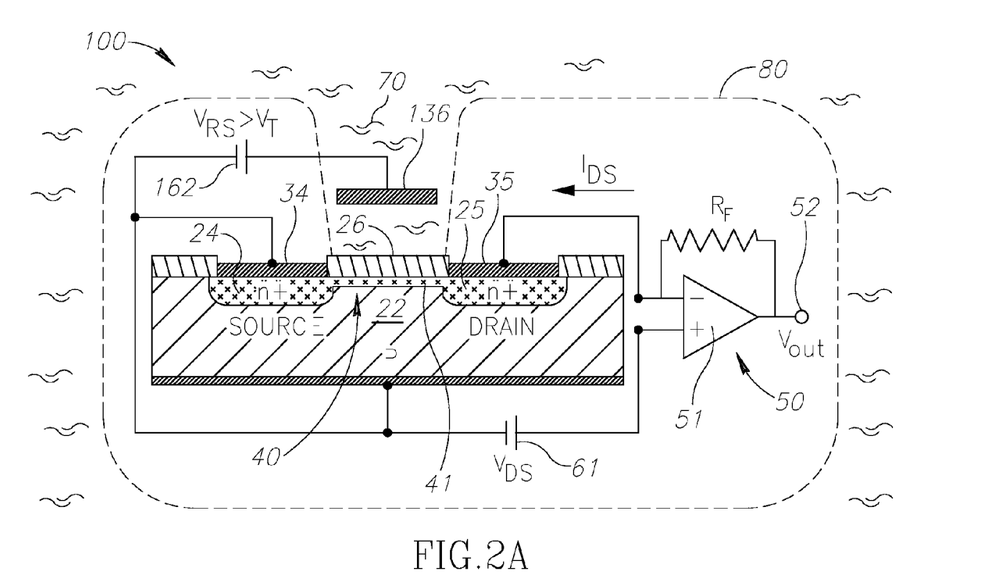
FIGS. 2A and 2B schematically illustrate a conventional ISFET and its operation.
Figure 2B:
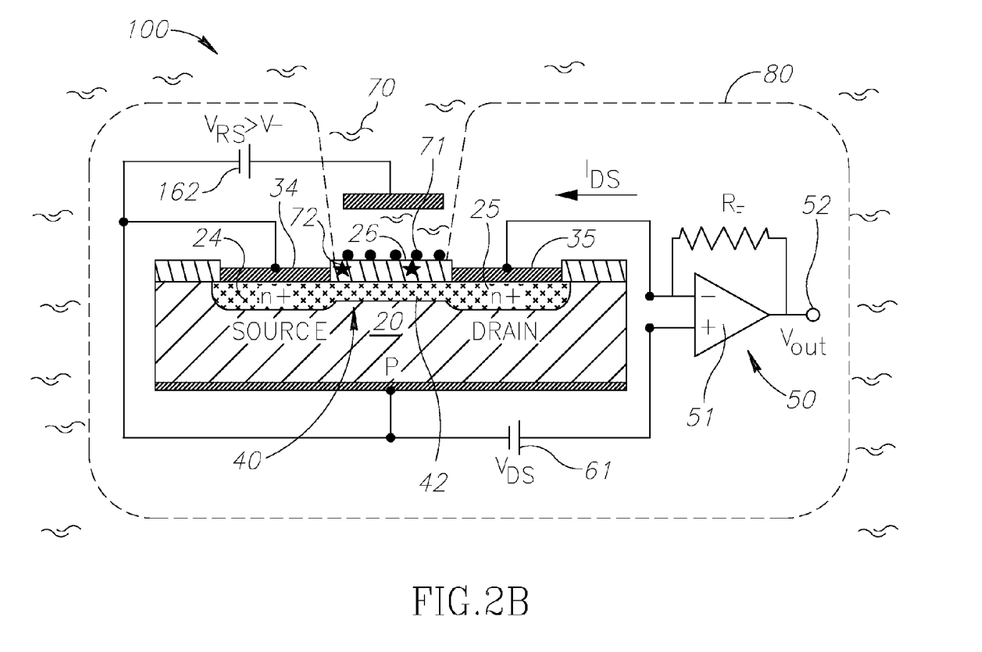

FIGS. 2A and 2B schematically show a conventional ISFET 100 operating to determine concentration $\rho_T$ of target ions in a fluid represented by wavy lines 70 in which ISFET 100 is assumed to be immersed.

ISFET 100 is optionally similar to MOSFET 20 except that ISFET 100 does not have a gate electrode 36, which in MOSFET 20 is located on channel insulator 26. Instead, ISFET 100 comprises a reference electrode 136 that is displaced from channel insulator 26 and is maintained at a voltage $V_{RS}$ relative to substrate 22 by a power supply 162. Channel insulator 26 may be left uncovered and configured to preferentially accumulate target ions so that it functions as an accumulator of ISFET 100. Alternatively, channel insulator 26 may be covered by a layer of material, which may function as an accumulator on which the target ions preferentially accumulate. In FIGS. 2A and 2B channel insulator 26 is shown uncovered, by way of example under an assumption that the insulator is operating as an accumulator. ISFET 100 optionally comprises a readout circuit 50 that generates voltage $V_{out}$ at output terminal 52 that is a function of current $I_{DS}$ between drain 25 and source 24. An insulating resin represented by a border 80 encapsulates all of ISFET 100 except for channel insulator 26 and reference electrode 136, which are exposed to fluid 70. Resin 80 protects elements of ISFET 100 from components of fluid 70 that might damage the elements.

In FIGS. 2A and 2B it is assumed that $V_{RS}$ is determined to have a magnitude that generates an electric field in channel region 40 sufficient to produce a current channel 41 in the channel region in the absence of accumulated target ions on channel insulator 26. FIG. 2A schematically shows ISFET 100 without ions accumulated on channel insulator 26 and a current channel 41 generated responsive to voltage $V_{RS}$.

FIG. 2B schematically shows ISFET 100 following accumulation of a given quantity of positive target ions 71, from fluid 70. By way of example, ISFET 100 is assumed to be used to determine pH of fluid 70 and positive ions 71 are assumed to be H+ ions. As a result of accumulation of the given quantity of positive ions 71 on channel insulator 26, potential of the channel insulator increases relative to substrate 22 and intensity of an electric field in channel region 40 is increased relative to the electric field generated by $V_{RS}$. The increased electric field generates a current channel 42, shown in FIG. 2A enlarged relative to current channel 41, that has a conductance greater than that of current channel 41. The increased conductance generates a corresponding increase in current $I_{DS}$ between drain 25 and source 24. Readout circuit 50 produces an output voltage $V_{out}$ responsive to the increased current, which may be used to determine the given quantity of positive ions 71 accumulated on channel insulator 26. The determined quantity of positive ions 71 may be used to estimate concentration $\rho_T$ of H+ ions and the pH of fluid 70.

Let $V^*_{RS}$ represent potential of channel insulator 26 relative to substrate 22 resulting from voltage $V_{RS}$. Let $Q_I$ represent "accumulated charge" that a quantity of target ions 71 accumulated by channel insulator 26 deposits on the insulator, and let $\Delta V(Q_I)$ represent a change in the potential of channel insulator 26 relative to substrate 22 generated by $Q_I$. Then current $I_{DS}$ between drain 25 and source 24 may be approximated by a function, generally linear or quadratic, of $(V^*_{RS}+\Delta V(Q_I)-V_T)$. If $V^*_{RS}$ is constant and $\Delta V(Q_I)$ is a known function of $Q_I$, then $V_{out}$ may be used to determine $\Delta V(Q_I)$, which in turn may be used to determine $Q_I$ and therefrom $\rho_T$.

Accuracy and precision of measurements of target ion concentration $\rho_T$ provided by ISFET 100 are a function of how well changes in accumulated charge $Q_I$ correlate with changes in target ion concentration. Variations in voltage $V^*_{RS}$ due to instabilities in voltage $V_{RS}$ provided by power supply 162, and changes in the work functions of fluid 70 and/or channel insulator 26 tend to degrade fidelity with which $Q_I$ tracks $\rho_T$. Ions, schematically represented by star icons 72 in FIG. 2A, that are accumulated by channel insulator 26 and subsequently trapped by the insulator introduce biases in accumulated charge $Q_I$ that degrades measurement of $\rho_T$. Once trapped by channel insulator 26, ions 72, which may be target ions or other ions present in fluid 70, are not readily returned to fluid 70 and may for example, introduce hysteresis to $Q_I$ as a function of $\rho_T$ that generates error in measurements of $\rho_T$ provided by ISFET 100.

By way of a simple example, assume channel insulator 26 accumulates a given quantity of target ions and corresponding accumulated charge $Q_I1$ at time $t_1$ when $\rho_T$ is equal to $\rho_T1$ and that at time $t_1$ traps a quantity of the accumulated ions having total trapped charge $Q_T$. Assume further that at a time $t_2$ $\rho_T$ has increased from $\rho_T1$ to $\rho_T2$, and at time $t_3$ $\rho_T$ has decreased back to the value, $\rho_T1$, that it had at time $t_1$. However, as a result of trapping of ions at time $t_1$, at time $t_3$ accumulated charge $Q_I$ will in general not return to $Q_I1$ but will have a value $(Q_I1+Q_T)$. If in response to accumulated charge $Q_I1$ at time $t_1$, ISFET 100 provides a measurement for $\rho_T$ equal to $\rho_T1$, at time $t_3$ the ISFET provides a value, $\rho_T3$, for $\rho_T$ in response to accumulated charge $(Q_I1+Q_T)$, which is not equal to the actual concentration $\rho_T1$ and is erroneous.

It is noted that an amount of trapped ions and corresponding trapped charge $Q_T$ may change over time and that leakage currents between reference electrode 136 and substrate 22 may deposit various amounts of "leakage" charge in channel insulator 26 that introduces error in measurements of $\rho_T$. As a result, conventional ISFETs such as ISFET 100 may require relatively frequent calibration to maintain satisfactory operation.

Figure 3:
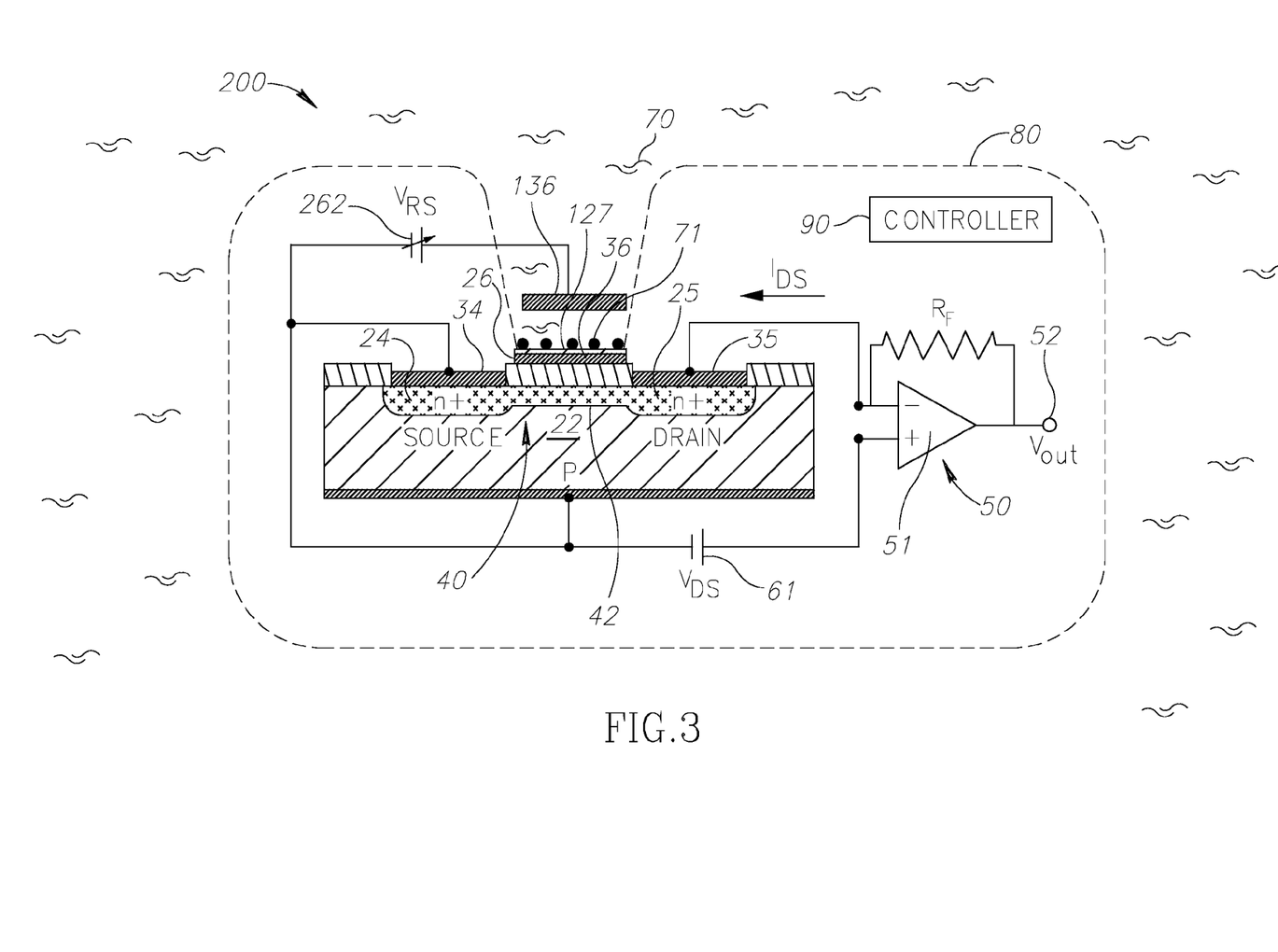
FIG. 3 schematically shows an ISFET detector, in accordance with an embodiment of the invention.

FIG. 3 schematically shows an ISFET detector 200 operating to determine concentration $\rho_T$ of a target ion in fluid 70, in accordance with an embodiment of the invention.

ISFET detector 200 optionally has features in common with ISFET 100, but unlike ISFET 100, ISFET detector 200 comprises a gate electrode 36 located on channel insulator 26 and a relatively thin accumulator 127 formed on the gate electrode, which functions as an accumulator base. A reference electrode 136 is connected to a power supply 262 that applies voltage $V_{RS}$ between the reference electrode and substrate 22. In an embodiment of the invention, power supply 162 is, as schematically shown in FIG. 3, a variable power supply controllable to vary voltage $V_{RS}$. Optionally, ISFET detector 200 comprises a controller 90 that controls power supply 162.

In an embodiment of the invention, accumulator 127 is a layer formed on gate electrode 36 from a dielectric insulating material, having thickness less than or equal to about 2 nm. Optionally, the accumulator has thickness less than or equal to about 1 nm. In an embodiment of the invention, the accumulator is substantially a monolayer of atoms or molecules formed on the gate electrode. The accumulator may be a naturally formed native oxide of a conducting material from which gate electrode 36 is formed or an artificially formed layer of material deposited on the gate electrode. By way of example, gate electrode 36 may be formed from titanium (Ti), antimony (Sb), or a noble metal such as gold (Au), platinum (Pt). Optionally, the gate electrode is formed from a highly doped polysilicon, such as a polysilicon having doping impurities in a concentration greater than or equal to about $10^{19}$ impurities per $cm^3$. Accumulator 127 may be a naturally or artificially formed native oxide of the conducting material from which the gate electrode is formed.

In an embodiment of the invention, to acquire a measurement of concentration $\rho_T$ of the target ion in fluid 70, controller 90 controls power supply 262 to apply a stable voltage $V_{RS}$ greater than a threshold voltage $V_T$ to generate a current channel between drain 25 and source 24 and accumulate a quantity of the target ions on accumulator 127. In FIG. 3 ISFET detector 200 is shown acquiring a measurement of $\rho_T$ and having accumulated a quantity of target ions 71 on accumulator 127. Assume that accumulated target ions 71 are positive and that they deposit a given amount of positive charge $Q_I$ on accumulator 127 that increases potential of accumulator 127 by an amount $\Delta V(Q_I)$ relative to a potential $V^*_{RS}$ of the accumulator generated by $V_{RS}$ in the absence of $Q_I$.

The potential change $\Delta V(Q_I)$ generates an enhanced current channel 42 in channel region 40 and a corresponding increase in current $I_{DS}$. Optionally, as in ISFET 100 (FIG. 2B), ISFET detector 200 comprises a readout circuit 50 which produces a signal $V_{out}$ responsive to the change in $I_{DS}$ that may be used to determine $Q_I$ and estimate $\rho_T$. However, in comparison to ISFET 100, ISFET detector 200 exhibits, reduced ion trapping and relatively little, if any hysteresis of $Q_I$ as a function of $\rho_T$. As a result ISFET detector 200 provides measurements of $\rho_T$ that are generally more accurate and precise than ISFET 100. The reduced ion trapping exhibited by ISFET detector 200 is indicated in FIG. 3 by absence of trapped ions 72 which are shown in FIG. 2B for ISFET 100.

In an embodiment of the invention, controller 90 controls power supply 262 to set potential $V_{RS}$ substantially equal to zero or disconnects power supply 262 from reference electrode 236 for a period of time, "$\tau_{RP}$", referred to as a reset period, prior to setting $V_{RS}$ to an operating voltage to acquire a measurement of $\rho_T$. Let "$\tau_{RT}$", represent a relaxation time that characterizes a rate at which trapped charge and/or leakage charge in accumulator 127 dissipates. In an embodiment of the invention, $\tau_{RP}$ is sufficiently longer than $\tau_{RT}$ so that at a time at which a measurement of $\rho_T$ is acquired by ISFET detector 200 an amount of trapped and/or leakage charge in accumulator 127 is relatively small and measurements of $\rho_T$ at different times are acquired for substantially same initial conditions of accumulator 127.

Figure 4:
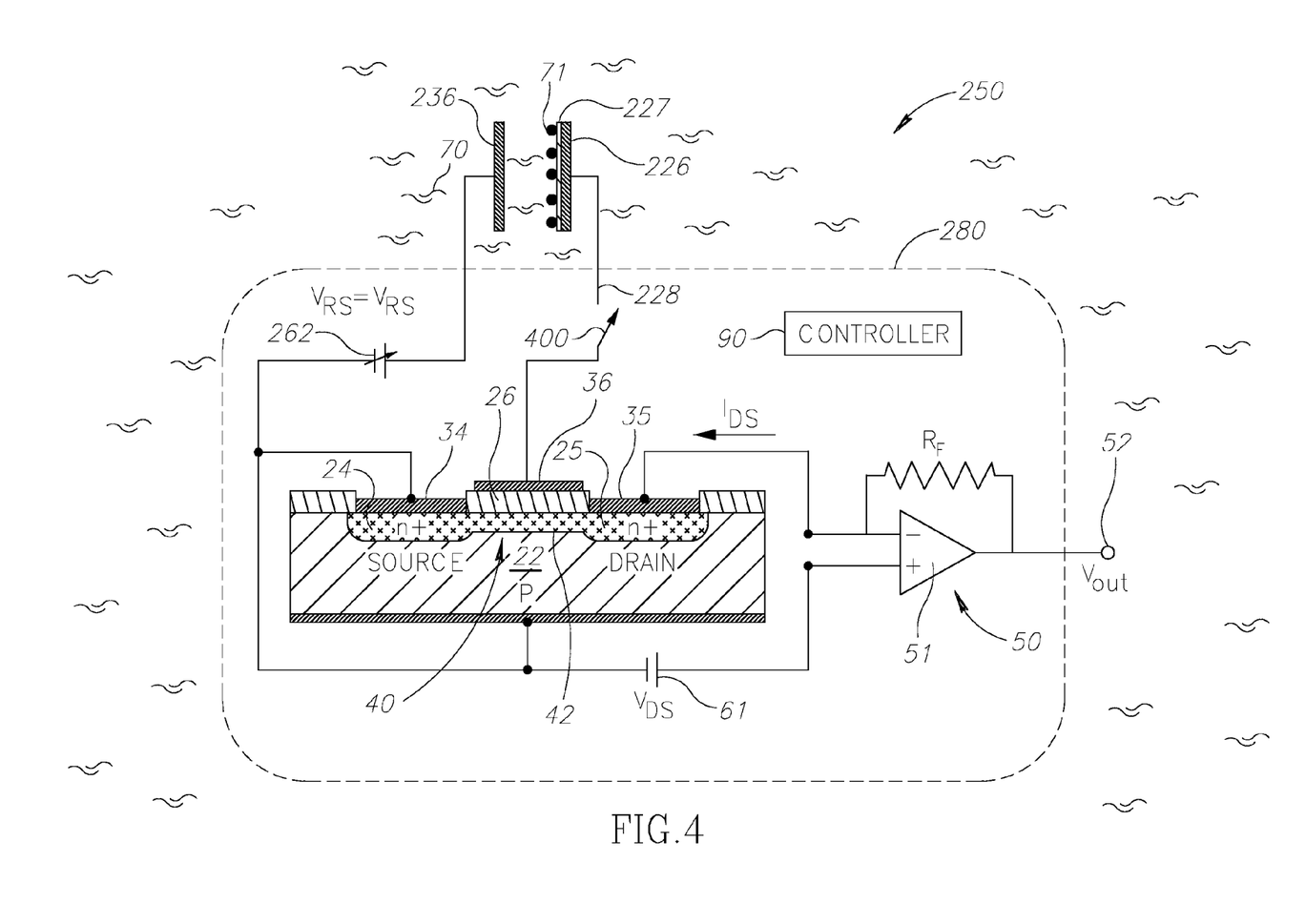
FIG. 4 schematically shows another ISFET detector comprising an antenna accumulator, in accordance with an embodiment of the invention.

FIG. 4 schematically shows an ISFET detector 250 comprising an antenna accumulator 227 acquiring measurements of concentration $\rho_T$ for a target ion in fluid 70, in accordance with an embodiment of the invention.

ISFET detector 250 is similar to ISFET detector 200, but unlike detector 200 that has its accumulator 127 formed on gate electrode 36, which functions as an accumulator base in ISFET 200, antenna accumulator 227 is not formed on gate electrode 36. Antenna accumulator 227 is formed on a conducting accumulator base 226, which is separate from, and connected to gate electrode 36 by a conducting element 228. The accumulator may be a naturally formed or artificially formed native oxide of a conducting material from which accumulator base 226 is made. By way of example, material accumulator base 226 may be formed from titanium (Ti), antimony (Sb), a noble metal such as gold (Au), platinum (Pt), or a highly doped polysilicon having doping impurities in a concentration greater than or equal to about $10^{19}$ impurities per $cm^3$. Accumulator 127 may be a naturally or artificially formed native oxide of the conducting material from which the gate electrode is formed. A protective encapsulating resin 280 optionally encapsulates components of ISFET detector 250 that may suffer damage from immersion in fluid 70 but does not encapsulate antenna accumulator 227 and a reference electrode 236. An optionally variable power supply 262 generates a potential difference between the reference electrode and substrate 22.

Separating antenna accumulator 227 from gate electrode 36 simplifies forming encapsulating resin 280 that protects elements of ISFET detector 250. Components such as source, drain, and gate electrodes 34, 35 and 36, and channel insulator 26 of ISFET detectors in accordance with embodiments of the invention, as well as corresponding components of conventional ISFETs, are relatively small, submicron features that are typically separated from each other by submicron distances. Encapsulating source and drain regions in a protective resin while leaving a channel oxide in a conventional ISFET, or a gate electrode of an ISFET detector in an embodiment of the invention exposed, generally requires high spatial resolution masking and etching processes. Masking and etching processes usually add to the expense and complexity of manufacturing the ISFET or ISFET detector.

By distancing antenna accumulator 227 from gate electrode 26 of ISFET detector 250 and thereby from submicron size features of the ISFET detector resin 280 may be formed using relatively inexpensive, low spatial resolution coating methods, such as dipping or spraying processes. Separating antenna accumulator 227 from gate electrode 36 in accordance with an embodiment of the invention also decouples antenna accumulator 227 from design constraints that may be mandated by features of ISFET Detector 250, such as size and shape of gate electrode 36 or proximity and size of source and drain electrodes 34 and 35.

Whereas in ISFET detector 250 as in ISFET 200 controller 90 may control power supply 262 to set $V_{RS}$ substantially equal to zero or disconnect the power supply from reference electrode 236 to allow trapped and/or leakage charge to dissipate. However, in some embodiments of the invention, ISFET detector 250 comprises a switch 400 operable to selectively connect accumulator base 226 to gate electrode 36 or electrically disconnect the accumulator base from the gate electrode. Optionally controller 90 controls switch 400 to disconnect accumulator base 226 from the gate electrode to allow trapped and/or leakage charge to dissipate. In an ISFET in accordance with an embodiment of the invention similar to ISFET 250 drift in measurements of pH have been reduced by as much as 50% by disconnecting accumulator base 227 from gate electrode 236 for a period of about an hour prior to acquiring a measurement of pH.

Figure 5:
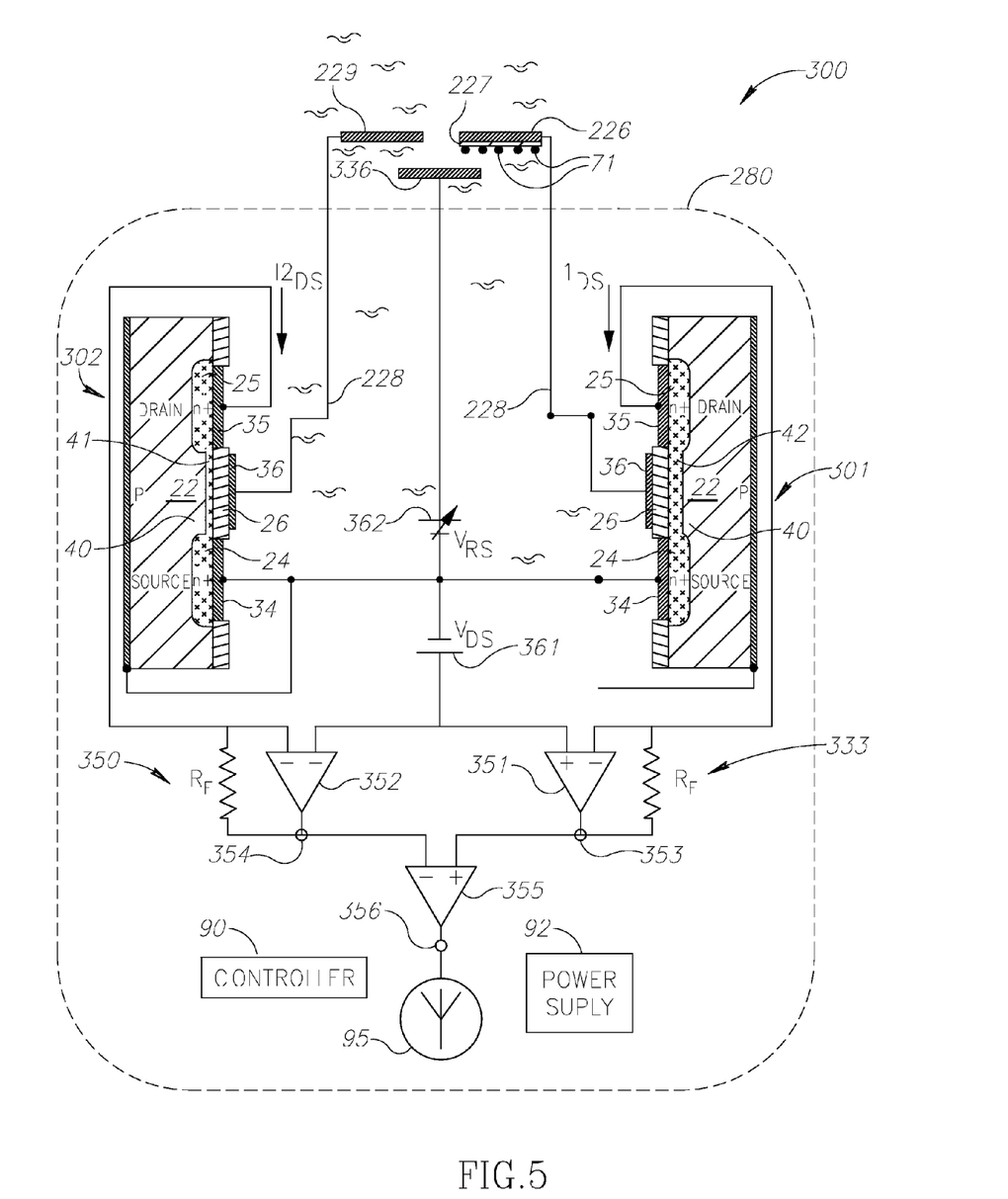
FIG. 5 schematically shows a dual ISFET detector, in accordance with an embodiment of the invention.

FIG. 5 schematically shows a dual ISFET 300 acquiring measurements of concentration $\rho_T$ of target ions in fluid 70, in accordance with an embodiment of the invention. Dual ISFET 300 optionally comprises two ISFET detectors 301 and 302 that are similar to ISFET detector 250 (FIG. 4) and a same reference electrode 336 that is common to both ISFETs. A power supply 362 applies an optionally variable voltage $V_{RS}$ to reference electrode 336. Optionally, a controller 90 controls power supply 362 to vary voltage $V_{RS}$ as described above and periodically set $V_{RS}$ to substantially zero. In an embodiment of the invention ISFET detectors 301 and 302 are configured so that a signal that is a difference between signals that they provide is substantially independent of factors that are not a function of $\rho_T$ and is used to determine $\rho_T$.

In an embodiment of the invention to configure ISFET detectors 301 and 302 to provide the difference signal, gate electrode 36 of ISFET detector 301 is electrically coupled to an accumulator base 226 having an antenna accumulator 227 characterized by a first sensitivity for accumulating target ions. Gate electrode 36 of ISFET detector 302 is optionally coupled to an accumulator base 229 identical to accumulator base 226, which is absent an accumulator that accumulates target ions or has an accumulator characterized by a second sensitivity for accumulating target ions that is different from that of the first sensitivity. As a result, potential of gate electrode 36 in ISFET detector 301 is affected by and is a function of concentration $\rho_T$ while potential of gate electrode 36 in ISFET detector 302 is relatively independent of $\rho_T$.

By way of example, accumulator base 229 is assumed not to have an accumulator that accumulates target ions and in FIG. 5 accumulator 227 is schematically shown having attracted and accumulated target ions 71 and accumulator base 229 is shown not having accumulated target ions. Accumulated ions 71 on accumulator 227 increase potential of gate electrode 36 comprised in ISFET detector 301 and generate an enhanced current channel 42 in ISFET detector 301 having conductance greater than that of a current channel generated substantially only responsive to potential $V_{RS}$. On the other hand gate electrode 36 in ISFET detector 302 is substantially unaffected by $\rho_T$, and ISFET detector 302 has a current channel 41 generated responsive to $V_{RS}$ that is substantially not enhanced by $\rho_T$.

In an embodiment of the invention, ISFET detectors 301 and 302 are coupled to a readout circuit 333 comprising substantially identical operational amplifiers 351 and 352 having optionally same feedback resistors $R_F$, and a difference amplifier 356. Operational, amplifiers 351 and 352 may be coupled to a same power supply 361 and generate a substantially same potential difference $V_{DS}$ between source electrode 34 and drain electrode 35 of each ISFET detector 301 and 302.

Operational amplifier 351 generates output signals responsive to potential of gate electrode 36 comprised in ISFET detector 301 at an output terminal 353 of the operational amplifier. Operational amplifier 352 generates output signals responsive to potential of gate electrode 36 comprised in ISFET detector 302 at an output terminal 354 of the operational amplifier. In an embodiment, output terminals 353 and 354 are connected to input terminals of difference amplifier 355. The difference amplifier generates difference signals at an output terminal 356 that are responsive to a difference between the signals provided at output terminals 353 and 354. The difference signals are substantially independent of variances in electric fields generated responsive to potential $V_{RS}$ in their respective channel regions 40 and may be used to determine the concentration $\rho_T$ of target ions in fluid 70.

In an embodiment of the invention, dual ISFET 300 comprises a transceiver 95 that is connected to output terminal 356 and receives difference signals provided by difference amplifier at the output terminal. The transceiver transmits signals responsive to the received difference signals that may be used to determine concentration $\rho_T$. Optionally, dual ISFET 300 comprises a power supply 92 that provides power to transceiver 95 and may itself receive energy by wireless electromagnetic or acoustic transmission. In an embodiment of the invention a protective coating 280 encapsulates components of dual ISFET 300 but leaves accumulator bases 229 and 226 and antenna accumulator 227 formed on accumulator base 226 exposed. Optionally dual ISFET 300 is monolithically formed in and on a suitable semiconductor substrate.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. An ISFET detector for determining concentration of target ions in a fluid, the ISFET detector comprising:
   a transistor comprising:
      a semiconductor substrate comprising a source and a drain having source and drain electrodes respectively and a channel region between them in the semiconductor substrate;
      an insulating material overlying the channel region; and
      a gate electrode formed on the insulating material;
   a reference electrode electrifiable to establish an electric field in the channel region;
   a conducting layer comprising an electrically conducting material;
   an accumulator layer formed on the conducting layer, the accumulator layer comprising a layer of material of thickness less than or equal to about 2 nm (nanometers) that accumulates target ions responsive to a concentration of the target ions in the fluid; and
   a conducting element comprising a switch selectively operable to electrically connect the conducting layer to, or disconnect the conducting layer from, the gate electrode.

2. An ISFET detector according to claim 1 wherein thickness of the accumulator layer is less than or equal to about 1 nm.

3. An ISFET detector according to claim 1 wherein the layer of material of the accumulator layer comprises a monolayer.

4. An ISFET detector according to claim 1 wherein the layer of material comprised in the accumulator layer has thickness substantially equal to that of a single atomic or molecular monolayer.

5. An ISFET detector according to claim 1 wherein the conducting layer comprises a metal.

6. An ISFET detector according to claim 1 wherein the conducting layer is formed from a polysilicon having a concentration of doping impurities greater than about $10^{19}$ impurities per $cm^3$.

7. An ISFET detector according to claim 1 wherein the layer of material comprised in the accumulator layer comprises a native oxide of the electrically conducting material on which the accumulator layer is formed.

8. An ISFET detector according to claim 1 comprising a controller that controls the switch to disconnect the conducting layer from the gate electrode until a time at which the accumulator layer accumulates target ions to determine concentration of the target ions in the fluid, at which time the controller controls the switch to connect the conducting layer to the gate electrode.

9. An ISFET detector according to claim 1 comprising a power supply electrically connected to the reference electrode and the semiconductor substrate that generates a potential difference between the reference electrode and the semiconductor substrate for a period of time during which the accumulator layer accumulates target ions to determine the concentration of the target ions.

10. Apparatus for determining concentration of target ions in a fluid, the apparatus comprising:
   first and second ISFET detectors according to any one of claims 2-7, 8, 9 and 1 having first and second accumulators respectively that accumulate first and second different quantities of target ions responsive to a same concentration of target ions in the fluid;
   circuitry that generates first and second signals responsive to the first and second quantities; and
   circuitry that generates a difference signal responsive to a difference between the first and second signals.

* * * * *